United States Patent [19]
Vuorinen et al.

[11] Patent Number: 5,213,966
[45] Date of Patent: May 25, 1993

[54] QUANTITATIVE DETERMINATION OF GLUCOSE UTILIZING ENZYME CASCADE SYSTEM

[75] Inventors: Pauli Vuorinen; Aimo Harmoinen; Hannu Jokela, all of Tampere, Finland

[73] Assignee: Kone Oy, Helsinki, Finland

[21] Appl. No.: 411,879

[22] Filed: Sep. 25, 1989

[30] Foreign Application Priority Data

Sep. 26, 1988 [FI] Finland .................. 884411

[51] Int. Cl.$^5$ .................. C12Q 1/54
[52] U.S. Cl. .................. 435/14; 435/4; 435/5; 435/15; 435/18; 435/25; 435/26; 436/68; 436/95; 436/164; 436/815
[58] Field of Search ........... 435/4, 5, 14, 34, 15, 435/18, 25, 26; 436/501, 68, 95, 164, 815

[56] References Cited

U.S. PATENT DOCUMENTS

| | | |
|---|---|---|
| 3,977,944 | 8/1976 | Muller-Mallhesius et al. .................. 195/103.5 R |
| 4,299,916 | 11/1981 | Litman et al. .................. 435/6 |
| 5,037,738 | 8/1991 | Lamos et al. .................. 435/12 |

FOREIGN PATENT DOCUMENTS 1212022 1/1984 Canada .
1212022 9/1986 Canada .

Primary Examiner—Margaret Moskowitz
Assistant Examiner—Ardin H. Marschel
Attorney, Agent, or Firm—Dennison, Meserole, Pollack & Scheiner

[57] ABSTRACT

A procedure is disclosed for the determination of glucose in a biological liquid, as well as a reagent mixture for use in conjunction with the procedure. The biological liquids concerned are especially blood, blood components, urine and spinal fluid. The procedure is based on a two-phase enzymatic reaction, the first phase of which comprises transforming glucose with the aid of ATP (adenosine-5-triphosphate) and hexokinase into glucose-6-phosphate and the second phase of which comprises transforming glucose-6-phosphate with the aid of NAD and glucose-6-phosphate dehydrogenase into 6-phosphogluconate. ATP, NAD and the enzymes mentioned are included in a suitably buffered reagent mixture, which can be added as a single dose to the glucose-containing liquid sample. The reaction is monitored kinetically by measuring the absorption caused by the NADH produced in the second phase twice within approximately one minute from the initiation of the first reaction phase. The glucose content of the sample can be calculated from the measured change of absorbance.

10 Claims, 2 Drawing Sheets

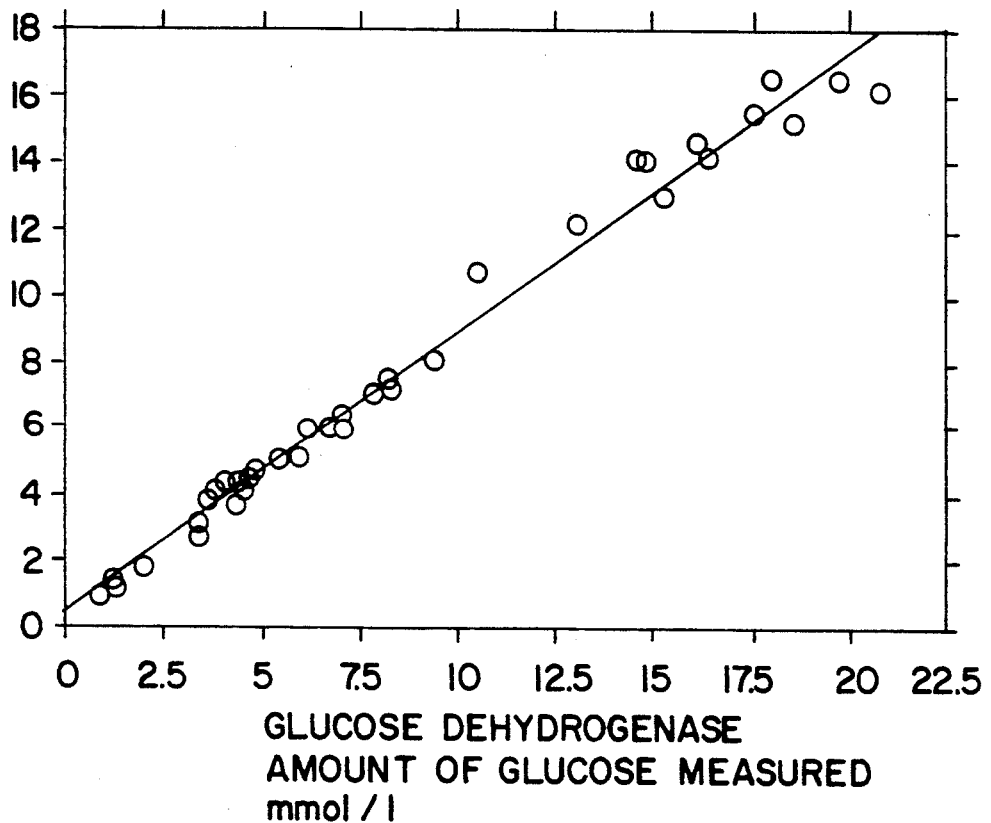
FIG.2 KINETIC HEXOKINASE AMOUNT OF GLUCOSE MEASURED mmol/l
GLUCOSE DEHYDROGENASE AMOUNT OF GLUCOSE MEASURED mmol/l

QUANTITATIVE DETERMINATION OF GLUCOSE UTILIZING ENZYME CASCADE SYSTEM

BACKGROUND OF THE INVENTION

The present invention relates to a procedure for the determination of glucose in a biological liquid, whereby reagents producing enzymatic reactions are added to a liquid sample containing glucose and the absorbance of the liquid is measured so that the amount of glucose can be calculated from the observed change of absorbance.

The biological liquids concerned include human and animal blood and their components, e.g. blood plasma and blood serum, and other liquids in the human organism, e.g. urine and spinal fluid.

The monitoring of the enzymatic reactions of glucose is based on the fact that such reactions produce a compound that absorbs light of a certain wavelength, thus increasing the absorbance of the reaction mixture at the wavelength in question. The glucose concentration in the liquid sample can be calculated from the difference between the absorbance values measured at the start and at the end of the reaction.

SUMMARY OF THE INVENTION

The glucose determination methods used hitherto are based on absorbance measurements at the reaction end points as mentioned above. By contrast, an object of the present invention is to provide a procedure that allows the glucose concentration in a liquid sample to be determined kinetically by measuring the absorption of the liquid at certain intervals during the course of the reaction.

Accordingly, one aspect of the invention provides a procedure for the determination of glucose in a biological liquid, which comprises adding reagents producing enzymatic reactions to a liquid sample containing glucose and measuring the absorbance of the liquid so that the amount of glucose can be calculated from the observed change of absorbance, whereby a two-phase enzymatic reaction is effected, the first phase of which consists in transforming glucose with the aid of ATP (adenosine-5-triphosphate) and hexokinase into glucose-6-phosphate and the second phase in transforming glucose-6-phosphate with the aid of NAD (nicotinamide-adenine-dinucleotide) and glucose-6-phosphate dehydrogenase into 6-phosphogluconate, the initial concentration of ATP being so high that only a small part of the ATP is spent in the first phase and the remaining ATP, with almost the original concentration, decelerates the second phase, and monitoring the reaction kinetically by measuring the absorption caused by the NADH (nicotinamide-adenine-dinucleotide, reduced form) produced in the second reaction phase twice within a period of approximately one minute from the initiation of the first reaction phase.

Thus, the kinetic glucose determination of the invention is characterized in that a two-phase enzymatic reaction is effected. The first phase consists of transforming glucose with the aid of ATP (adenosine-5-triphosphate) and hexokinase into glucose-6-phosphate and the second phase consists of transforming glucose-6-phosphate with the aid of NAD (nicotinamide-adeninedinucleotide) and glucose-6-phosphate dehydrogenase into 6-phosphogluconate. The reaction is monitored kinetically by measuring the absorption caused by the NADH produced in the second reaction phase twice within a period of approximately one minute from the initiation of the first reaction phase.

DETAILED DESCRIPTION OF THE INVENTION

The reaction phases on which the invention is based are as follows:

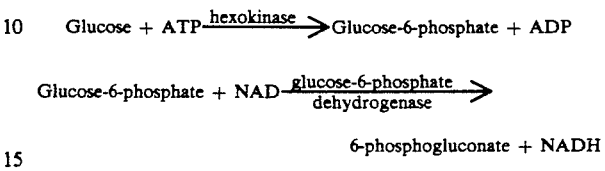

As can be seen from the reaction equations, the amount of NADH produced is directly proportional to the glucose concentration in the sample under analysis. NADH absorbs at wavelength 340 nm, and the glucose concentration can be calculated from the measured increase in the absorbance.

One of the advantages provided by the procedure of the invention is that it is considerably faster than the prior art method based on end-value measurement. In the procedure of the invention, the result of the determination is obtained within about one minute after the initiation of the reaction, whereas in the previously known method the result is only obtained after a delay of at least 5 minutes. In experiments applying the procedure of the invention, successful absorption measurements have been carried out within a time of from 35 to 50 seconds from the start of the reaction, but in practice even faster determination may be possible.

By virtue of the speed of the procedure, considerably larger numbers of samples can be analyzed than before, especially in automatic analyzers. However, the equipment used is not critical to the invention, because the measurements can be performed with any device capable of measuring the 340 nm wavelength and having a resolution sufficient for reliable detection of small differences in absorbance.

A further advantage of the invention is that the procedure is linear for glucose concentrations of from 1 to 40 mmol/l, i.e. for a wider range of concentrations than the prior art method based on end-value measurement. This reduces the need for dilution of samples with higher glucose concentrations before the determination.

Experiments have also shown that the procedure of the invention, unlike the known methods, is especially suited for the determination of the glucose content of whole-blood hemolysate. The hemolysate is obtained by mixing a blood sample directly with a hemolytic solution. With this procedure, the determination can be performed so quickly that the result is known almost immediately after the sample has been taken.

The invention also relates to a reagent mixture applicable in the glucose determination described above. The mixture is characterized in that it consists of a buffered water solution containing ATP, NAD, hexokinase and glucose-6-phosphate dehydrogenase, such solution being added in a single dose to each sample to be analyzed.

The reagent mixture of the invention suitably contains all the chemical components required for the determination of glucose, and the concentrations of different reagents in the mixture are so adjusted that the fast kinetic measurement implied by the invention becomes possible. Therefore, the concentration of ATP, in particular, should be sufficiently high, because this retards the second reaction phase, catalyzed by glucose-6-phosphate dehydrogenase, so that a kinetic measurement within about a minute from the start of the reaction becomes possible.

DESCRIPTION OF THE PREFERRED EMBODIMENTS

In a preferred composition of the reagent of the invention the ATP concentration is about 17 mmol/1, the NAD concentration about 5 mmol/1, hexokinase activity about 2500 U/1 and glucose-6-phosphate dehydrogenase activity about 2500 U/1. In addition to the components mentioned, the mixture may contain a tris-buffer in a concentration of about 0.25 mmol/1, in which case the mixture has a pH of about 7.5 and a magnesium salt concentration of about 5.25 mmol/1.

In use of the reagent mixture of the invention, a suitable mixing ratio of glucose-containing liquid sample and reagent mixture is 1/51. When this mixing ratio is observed, the enzyme activities in the reaction mixture containing the sample are approximately the same as in the reagent mixture, i.e. suitably about 2500 U/1. In the determination of glucose in whole-blood hemolysate, however, a suitable mixing ratio of sample and reagent mixture is 1/15. In this case, due to the increased amount of liquid, the enzyme activity values of the reaction mixture will be somewhat lower than those of the reagent mixture, amounting e.g. to about 2340 U/1.

BRIEF DESCRIPTION OF THE DRAWINGS

In the drawings:

FIG. 2 shows graphically the correlation between glucose concentration values obtained using the glucose dehydrogenase method and by the procedure of the invention.

TESTING OF THE PROCEDURE

Figure 1:
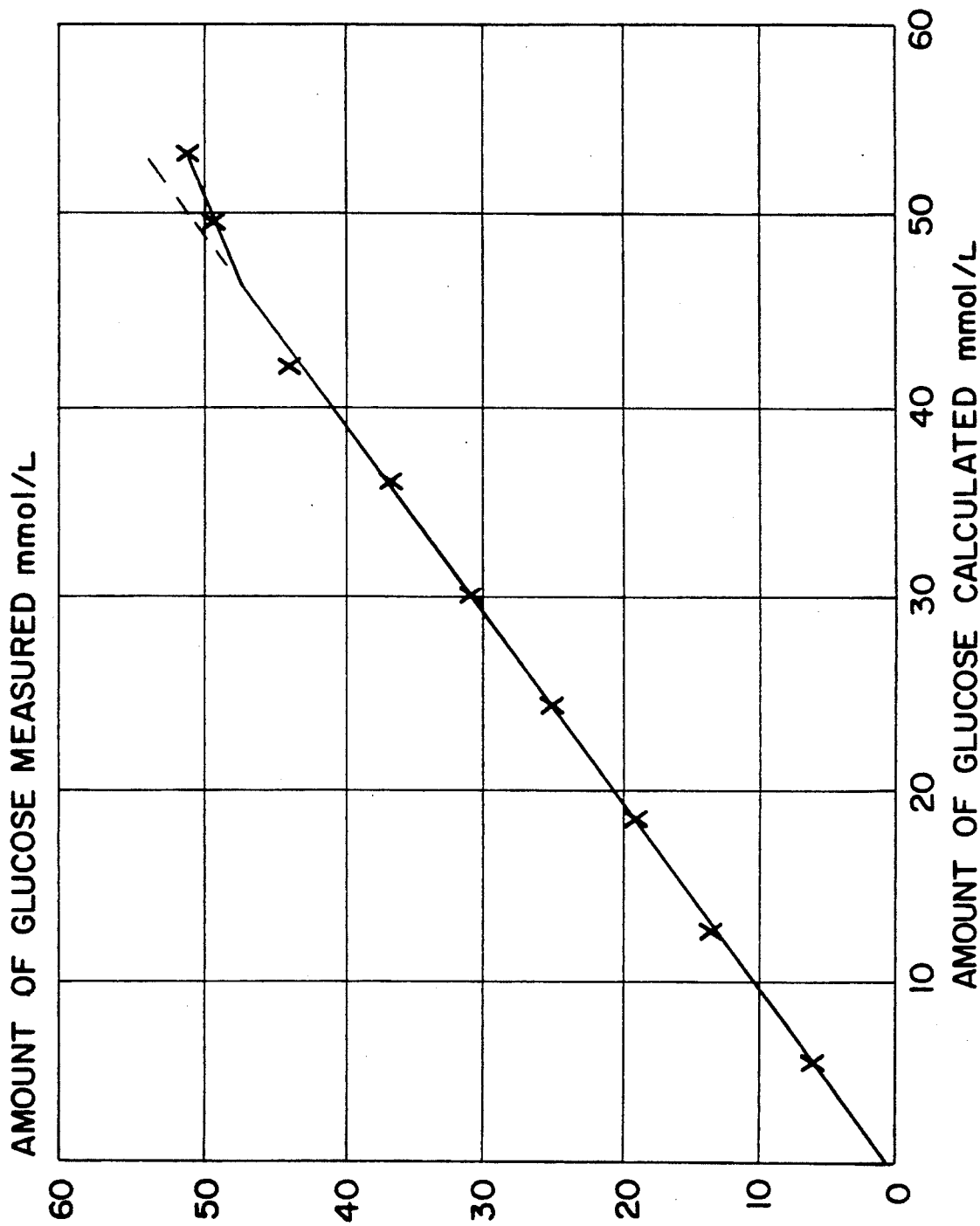
FIG. 1 compares graphically the glucose concentration values obtained by an embodiment of the inventive procedure with calculated glucose concentration values.

To test the linear measurement range and precision of the procedure of the invention, a serum having a known high glucose concentration was diluted with another serum having a known low glucose concentration. To each sample of the diluted serum was added a reagent mixture with pH 7.5 and the following composition: tris-buffer 0.25 mmol/1, magnesium salt 5.25 mmol/1, NAD 5.0 mmol/1, ATP 17.0 mmol/1, hexokinase 2500 U/1 and glucose-6-phosphate dehydrogenase 2500 U/1. In each case, the mixing ratio of sample to reagent mixture was 1/51. The series of diluted samples was measured at a temperature of 37.C using a Kone Dynamic apparatus by measuring the change in the absorbance of the reaction mixture in the case of each sample at a wavelength 340 nm and a time interval of 35 to 50 seconds from the start of the reaction. In the appended FIG. 1, the glucose concentration values obtained by the procedure of the invention from the changes of absorbance are compared to calculated glucose concentration values. The curve in the FIGURE shows that the linear measurement range of the procedure covers glucose concentration values from 1 to 40 mmol/1. Within this range, there is an excellent agreement between the measured results and the calculated glucose concentration values.

Furthermore, the reliability of the procedure of the invention regarding the determination of glucose in whole-blood hemolysate was tested by comparing results obtained by the procedure with results obtained by the known glucose dehydrogenase method. Forty samples of whole-blood hemolysate were prepared by pipetting 50 $\mu$l of whole blood into 1 ml of a hemolytic solution produced by Merck Oy. The glucose concentration in each sample was first measured by the glucose dehydrogenase method using Eppendorf's EPOS apparatus and then, using the prototype of a flow-through-based measuring apparatus made by Kone Oy, by the procedure of the invention. In each case the same reaction conditions were employed as in the testing of the linear measurement range as described above, except that the mixing ratio of sample and reagent mixture was 1/15. The appended FIG. 2 shows graphically the correlation between the results obtained by the two methods. The correlation line is y $=0.851x +0.341$; r $=0.993$. It can be seen from the results that the glucose concentration values obtained by the procedure of the invention are in very good agreement with those obtained by the glucose dehydrogenase method.

It will be obvious to a person skilled in the art that different embodiments of the invention are not restricted to the examples described above, but that they may instead by varied within the scope of the following claims.

We claim:

1. A process for quantitative determination of glucose in a biological liquid, comprising the steps:
   a) adding to the liquid a mixture of reagents comprising ATP in a concentration in a range of 15 to 20 mmol/1, hexokinase, NAD and glucose-6-phosphate dehydrogenase, to initiate a two phase enzymatic reaction, including
   a first phase in which glucose-6-phosphate reacts with NAD and glucose-6-phosphate dehydrogenase to form 6-phosphogluconate and NADH,
   said ATP in said concentration range being present in an amount sufficient that only a small portion thereof reacts with glucose in said first phase, and a remainder thereof is present during said second phase, said ATP remainder causing deceleration of said second phase;
   b) monitoring the kinetics of said reaction by measuring the light absorbance of said NADH twice within a period not exceeding about one minute from the initiation of said reaction; and
   c) calculating the glucose concentration in the liquid from the absorbance measurements taken during said period.

2. A process according to claim 1, wherein the absorption measurements are performed within a period of from 35 to 50 seconds from the initiation of the reaction.

3. A process according to claim 1, wherein the biological liquid is blood or a blood component.

4. A process according to claim 1, wherein the biological liquid is a whole-blood hemolysate.

5. A process according to claim 1, wherein the hexokinase in the reaction mixture has an activity at least approximately 2340 U/1.

6. A process according to claim 1, wherein the glucose-6-phosphate dehydrogenase in the reaction mixture has an activity at least approximately 2340 U/1.

7. A process according to claim 1, wherein the concentration of ATP in the reaction mixture is approximately 17 mmol/l.

8. A process according to claim 1, wherein reagent mixture is added in a single dose to a glucose-containing sample to be analyzed.

9. A reagent mixture for quantitative determination of glucose according to claim 1, which comprises a buffered water solution containing ATP, NAD, hexokinase and glucose-6-phosphate dehyyrogenase, said solution being suitable for being added in a single dose to each glucose-containing sample to be analyzed.

10. A reagent mixture according to claim 9, having an ATP concentration approximately 17 mmol/l, a NAD concentration approximately 5 mmol/l, a hexokinase activity approximately 2500 U/l and a glucose-6-phosphate dehydrogenase activity approximately 2500 U/l.

* * * * *